United States Patent [19]

Jones

[11] Patent Number: 5,424,416

[45] Date of Patent: Jun. 13, 1995

[54] PROCESS FOR PREPARATION OF 2-DEOXY-2,2-DIFLUORO-D-RIBOFURANO-SYL-3,5-HYDROXY PROTECTED-1-ALKYL AND ARYL SULFONATES AND THEIR USE IN PREPARATION OF 2',2'-DIFLUORO-2'-DEOXY NUCLEOSDIES

[75] Inventor: Charles D. Jones, Indianapolis, Ind.

[73] Assignee: Eli Lilly and Company, Indianapolis, Ind.

[21] Appl. No.: 111,578

[22] Filed: Aug. 25, 1993

[51] Int. Cl.$^6$ .......................... C07H 5/08; C07H 1/00; C07H 19/14; C07H 19/16

[52] U.S. Cl. .................. 536/27.11; 536/118; 536/125

[58] Field of Search ...................... 536/27.11, 118, 125

[56] References Cited

U.S. PATENT DOCUMENTS

| | | | |
|---|---|---|---|
| 3,282,921 | 11/1966 | Verheyden et al. | 536/27.14 |
| 4,145,531 | 3/1979 | Eckstein et al. | 536/27.11 |
| 4,211,773 | 7/1980 | Lopez et al. | 514/46 |
| 4,526,988 | 7/1985 | Hertel | 549/313 |
| 4,625,020 | 11/1986 | Brundidge et al. | 536/27.4 |
| 4,751,221 | 6/1988 | Watanabe et al. | 514/46 |
| 4,965,374 | 10/1990 | Chou et al. | 549/313 |

FOREIGN PATENT DOCUMENTS

| | | | |
|---|---|---|---|
| 145978 | 6/1985 | European Pat. Off. | . |
| 0184365 | 6/1986 | European Pat. Off. | 536/27.11 |
| 219829 | 10/1986 | European Pat. Off. | C07H 9/16 |
| 211354 | 2/1988 | European Pat. Off. | C07H 19/73 |
| 339161 | 4/1989 | European Pat. Off. | C07F 9/65 |
| 345751 | 6/1989 | European Pat. Off. | . |
| 428109 | 11/1989 | European Pat. Off. | . |
| 62-29527 | 2/1987 | Japan | 514/46 |
| 2125401 | 8/1983 | United Kingdom | . |

OTHER PUBLICATIONS

Watanabe et al., "Nucleosides. 110. Synthesis and Antiherpes Virus Activity of Some 2'-Fluoro-2'-deoxyarabinofuranosylpyrimidine Nucleosides," *J. Medicinal Chem.*, 22(1), 21–24 (1979).

Hertel et al., "Synthesis of 2-Deoxy-2,2-difluoro-D-ribose and 2-Deoxy-2,2-difluoro-D-ribofuranosyl Nucleosides," *J. Org. Chem.*, 53, 2406–2409 (1988).

Nishimura et al., "A New Synthetic Method of [for Making] Nucleosides," *Chem. Pharm. Bull.*, 11(11), 1470–1472 (1963).

Nishimura et al., "Studies on Synthetic Nucleosides. IV. A New Synthetic Method of Pyrimidine and Purine Ribosides," *Chem. Pharm. Bull.*, 12(2), 1471–1478 (1964).

Barton et al., *Comprehensive Organic Chemistry, The Synthesis and Reactions of Organic Compounds*, vol. 5, *Biological Compounds*, Pergamon Press, New York, 1979, 1979 & 22.2.3.1 (Condensation Reactions), see pp. 60–67.

Wittenburg, "Eine neue Synthese von Nucleosiden," *Z. Chem.*, 4(8), 303–304 (1964).

Vorbruggen, et al., *J. Org. Chem.*, 41, 2084 (1976).

Kazimierczuk, et al., *J. Am. Chem. Soc.*, 106, 6379–82 (1984).

Seela, et al., *Liebigs Ann. Chem.*, 895–901 (1989).

Reichman, et al., *Carbohydr. Res.*, 42, 233 (1975).

Howell, et al., *J. Org. Chem.*, 53, 85–88 (1988).

Davoll, et al., *J. Am. Chem. Soc.*, 73, 1650 (1951).

Hilbert, et al., *J. Am. Chem. Soc.*, 52, 2001 (1930).

Sanghvi, et al., *Nucleosides & Nucleotides*, 6(4), 761–774 (1987).

Koenigs, eta l., *Berichete Dent. Chem. Gesselschaft*, 34, 957–981.

Prystas, et al., *Coll. Czech. Chem. Comm.*, 31, 3990–4001 (1966).

Hoffer, et al., *Chem. Ber.*, 93, 2777–2781 (1960).

Wittenburg, et al., *Chem. Ber.*, 101, 1095–1114 (1968).

Howard, et al., *J. Am. Chem. Soc.*, 1052–1054 (1947).

Hertel, et al., *Nucleosides & Nucleotides*, 8(5&6), 951–955 (1989).

Hubbard, et al., *Nucleic Acid Research*, 12, 6827 (1984).

*Primary Examiner*—Douglas W. Robinson
*Assistant Examiner*—L. Eric Crane
*Attorney, Agent, or Firm*—David E. Boone

[57] ABSTRACT

A stereoselective process for preparing a β-anomer enriched 2-deoxy-2,2-difluoro-D-ribofuranosyl-3,5-hydroxy protected-1-alkyl and aryl sulfonate intermediates by contacting an α-anomer enriched 2-deoxy-2,2-difluoro-D- ribofuranosyl-3,5-hydroxy protected-1-fluoroalkyl and fluoroaryl sulfonate with a conjugate anion of a sulfonic acid containing the desired alkyl or aryl sulfonate.

12 Claims, No Drawings

PROCESS FOR PREPARATION OF 2-DEOXY-2,2-DIFLUORO-D-RIBOFURANOSYL-3,5-HYDROXY PROTECTED-1-ALKYL AND ARYL SULFONATES AND THEIR USE IN PREPARATION OF 2',2'-DIFLUORO-2'-DEOXY NUCLEOSDIES

BACKGROUND OF THE INVENTION

1. Field of the Invention

This invention pertains to the field of pharmaceutical chemistry and provides a stereoselective process for preparing β-anomer enriched 2-deoxy-2,2-difluo-D-ribofuranosyl-3,5-hydroxy blocked-1-alkyl and aryl sulfonate intermediates used in the preparation of known anit-cancer and anti-viral nucleoside agents.

2. State of the Art

Processes for preparing anti-cancer and anti-viral β-nucleoside agents involve the stereochemical inversion of furanose (carbohydrate) intermediates bearing a leaving group at the anomeric center. Therefore, when a β-anomer nucleoside is the desired product, an α-anomer enriched carbohydrate intermediate is preferably used in $S_N2$ coupling reactions.

The most frequently used coupling intermediate is 1-chloro-2-deoxy-3,5-(di-O-p-toluoyl)-α-D-erythropentofuranose, which was first prepared by Hofer, Chem. Ber., 93, 2777 (1960). This compound is crystalline and exists exclusively as an α-anomer. However, coupling reactions using Hofer's α-chloro anomer carbohydrate to prepare 2-deoxyribofuranosyl nucleosides were non-stereoselective. Hubbard, et. al., Nucleic Acids, 12, 6827 (1984) later studied Hofer's results and found that the α-chloro carbohydrate intermediate anomerized in the organic solvent used at ambient temperatures to form the corresponding β-chloro anomer carbohydrate intermediate. Therefore, anomerization was responsible for the non-stereoselective nature of Hofer's coupling reaction. Hubbard, et. al., evaluated the anomerization of the α-chloro carbohydrate in several solvents to find solvents that would hold the effects of anomerization to a minimum so that a high yield of the desired β-nucleoside product could be obtained.

Besides chloro, alkyl and aryl sulfonyloxys represent other types of leaving groups that have been evaluated. However, due to the instability of some 2-deoxy-D-erythropentofuranosyl sulfonate intermediates, carbohydrates that contain sulfonyloxy leaving groups are conspicuously absent from the chemical literature and are rarely used in coupling.

U.S. Pat. Nos. 4,526,988 and 4,965,374 teach coupling reactions that employ anomeric mixtures of 2-deoxy-2,2-difluoro-D-ribofuranosyl-1-alkyl and aryl sulfonate intermediates to make 2'-deoxy-2',2'-difluoronucleosides. As a consequence of using anomeric mixtures, these processes are non-stereoselective for β-anomer nucleosides and provide a 1:1 and 4:1 α to β anomer ratio respectively, of 2'-deoxy-2',2'-difluoronucleosides.

In order to improve the stereoselectivity of the coupling reactions used to make 2'-deoxy-2',2'-difluronucleosides, Chou, et. al., in Pending U.S. patent application Ser. No. 07/902,135, found that carbohydrate intermediates containing iodo, bromo and sulfonate leaving groups would stereoselectively couple under anionic coupling conditions and provide a β to α anomer nucleoside ratio as high as 10:1. The method for making the sulfonate intermediates used by Chou is taught by Chou, et. al., in Pending U.S. patent application Ser. No. 07/902,305. The method involves obtaining an α-anomer enriched 2-deoxy-2,2-difluoro-ribofuranosyl-3,5-hydroxy protected-1-alkyl and aryl sulfonate intermediates from their corresponding β-anomer enriched sulfonate intermediates by anomerizing β-anomer enriched sulfonate intermediate with the conjugate anion of a sulfonic acid of the sulfonate.

Chou, et. al., in Pending U.S. patent application Ser. No. 07/902,143, teach a method for obtaining β-anomer enriched 2-deoxy-2,2-difluoro-ribofuranosyl-3,5-hydroxy protected-1-aryl sulfonate intermediates from lactols. However, as α-anomers, these intermediates contain the wrong stereochemistry for providing β-anomer nucleoside by $S_N2$ coupling. Therefore, in order to use them in $S_N2$ coupling, β-anomer enriched carbohydrates must be converted to α-anomer enriched carbohydrates by equilibration.

Despite the foregoing advances, there continues to be a need for alternative stereoselective processes for preparing β-anomer enriched 2-deoxy-2,2-difluororibofuranosyl-3,5-hydroxy protected-1-alkyl and aryl sulfonate intermediates.

It is an object of the present invention to provide a stereoselective process for preparing β-anomer enriched 2-deoxy-2,2-difluoro-ribofuranosyl-3,5-hydroxy protected-1-alkyl and aryl sulfonate intermediates from highly reactive α-anomer enriched 2-deoxy-2,2-difluoro-ribofuranosyl-3,5-hydroxy protected-1-fluoroalkyl and fluoroaryl sulfonate intermediates.

Other objects and advantages of the present invention will become apparent from the following description of embodiments.

SUMMARY OF THE INVENTION

The present invention is a stereoselective process for preparing a β-anomer enriched carbohydrate of the formula

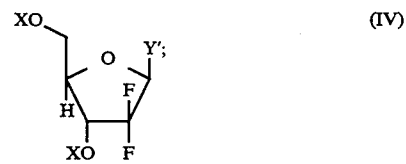

wherein each X is independently selected from hydroxy protecting groups; and Y' is an alkylsulfonyloxy or arylsulfonyloxy group; comprising contacting a compound of the formula

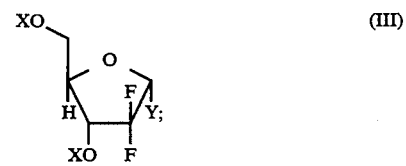

wherein X is as defined above and Y is a fluoroalkylsulfonyloxy or fluoroarylsulfonyloxy group; with a conjugate anion of a sulfonic acid, in an inert solvent, at elevated temperatures.

The present invention is also a stereoselective process for preparing a β-anomer enriched 2'-deoxy-2',2'-difluoronucleoside of the formula

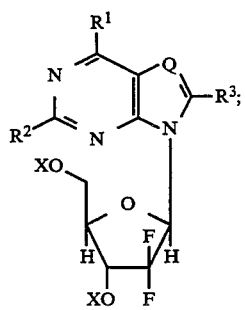
(I)

wherein X is as defined above; $R^1$, $R^2$ and $R^3$ are each independently selected from the group consisting of hydrogen, —OZ, —NHW, N(alkyl) W, halo, cyano, azido, alkoxy and thioalkyl; Q is selected from the group consisting of CH, $CR_4$ and N, wherein $R_4$ is halo, carboxamide, thiocarboxamide, alkoxycarbonyl and nitrile; where Z is a hydroxy protecting group and W is an amino protecting group; comprising contacting a lactol of the formula

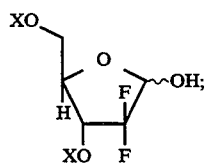
(II)

wherein X is as defined above; with a base in a low freezing inert solvent; lowering the temperature of the reaction mixture in the range of about —40° C. to about —120° C.; and adding a sulfonating reagent to form an α-anomer enriched carbohydrate of the formula

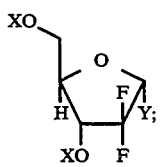
(III)

wherein X is as defined above and Y is a fluoroalkylsulfonyloxy or fluoroarylsulfonyloxy group; contacting the carbohydrate of formula (III) with a conjugate anion of a sulfonic acid, in an inert solvent, at elevated temperatures, to form a β-anomer enriched carbohydrate of the formula

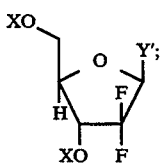
(IV)

wherein X is as defined above and Y' is an alkylsulfonyloxy or arylsulfonyloxy group; heating the carbohydrate of formula (IV) in the presence of a conjugate anion of a sulfonic acid for a time and at a temperature sufficient to form an α-anomer enriched carbohydrate of the formula

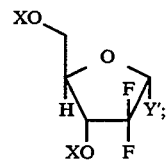
(V)

wherein X and Y' are as defined above; contacting the carbohydrate of formula (V) with an nucleobase anion of the formula

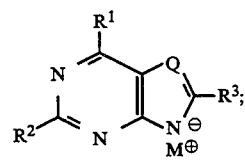
(VI)

wherein $R^1$, $R^2$, $R^3$ and Q are as defined above; and M is a metal cation; in an inert solvent; and heating for a time and at a temperature sufficient to form the β-anomer enriched 2-deoxy-2,2-difluoronucleoside of formula (I).

DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent.

The term "lactol" alone or in combination refers to a 2-deoxy-2,2-difluoro-3,5-hydroxy protected-D-ribofuranose. The term "carbohydrate" alone or in combination refers to an activated lactol wherein the C-1 hydroxy group has been replaced. The term "halo" alone or in combination refers to chloro, iodo, fluoro and bromo groups. The term "alkyl" alone or in combination refers to straight, cyclic and branched chain aliphatic hydrocarbon groups which preferably contain up to 7 carbon atoms, such as methyl, ethyl, n-propyl, isopropyl, n-butyl, t-butyl, n-pentyl, n-hexyl, 3-methylpentyl groups and the like or substituted straight, cyclic and branched chain aliphatic hydrocarbons, such as chloroethyl, 1,2-dichloroethyl, and the like. The term "alkoxy" alone or in combination refers to the general formula AO; wherein A is alkyl. The term "aryl" alone or in combination refers to general formula BS; wherein B is alkyl or hydrogen. The term "ester" alone or in combination refers to the carbocyclic or heterocyclic groups such as phenyl, naphthyl, thienyl and substituted derivatives thereof. The term "thioalkyl" alone or in combination refers to the general formula BS; wherein B is alkyl or hydrogen. The term "ester" alone or in combination refers to the general formula EOOC; wherein E is alkyl or aryl. The term "aromatic" alone or in combination refers to benzene like structures containing (4n +2) delocalized π electrons. The term "substituted" alone or in combination refers to substitution by at least one or more of the groups selected from cyano, halo, carboalkoxy, aryl, nitro, alkoxy and dialkylamino. The phrase "anomer enriched" alone or in combination refers to an anomeric mixture wherein the ratio of a specified anomer is greater than 1:1 and includes a substantially pure anomer.

The lactol starting materials of formula (II) are commonly known in the art and can be readily synthesized by standard techniques as described, for example, in U.S. Pat. No. 4,526,988 which teaches the synthesis of a 2-deoxy-2,2-difluoro-3,5-hydroxy protected-D-ribofuranose. In a preferred embodiment of the present process, 2-deoxy-2,2-difluoro-3,5-dibenzoate-D-ribofuranose is used as the lactol.

The present process requires protecting the hydroxy groups of the lactol of formula (II) to prevent undesirable side reactions. Hydroxy protecting groups (X) suitable for use in the present process may be chosen from protecting groups known in the art and commonly used in synthetic organic chemistry. These hydroxy protecting groups should preferably be capable of being efficiently placed on the lactol and easily removed therefrom once the reaction is complete. Hydroxy protecting groups known in the art are described in Chapter 3 of *Protective Groups in Organic Chemistry*, McOmie Ed., Plenum Press, New York (1973) and Chapter 2 of *Protective Groups in Organic Synthesis*, Green, John, J. Wiley and Sons, New York (198); preferred are ester forming groups such as formyl, acetyl, substituted acetyl, propionyl, butanoyl, pivaloyl, 2-chloroacetyl, benzoyl, substituted benzoyl, phenoxyacetyl, methoxyacetyl, carbonate derivatives such as phenoxycarbonyl, ethoxycarbonyl, t-butoxycarbonyl, benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisiloxyanyl; carbamates such as N-phenylcarbamate; however more preferred are benzoyl, mono-substituted benzoyl and disubstituted benozyl, acetyl, pivaloyl, triphenylmethyl ethers, and silyl ether forming groups, especially t-butyldimethylsilyl; while most preferred is benzoyl.

The reaction conditions employed in preparing the hydroxy protected lactol depend on the nature of the protecting groups chosen and are described in U.S. Pat. No. 4,526,988, incorporated herein by reference.

To obtain an efficient coupling reaction between the nucleobase anion and the carbohydrate, an appropriate leaving group must be stereoselectively attached at C-1 of the lactol to activate the lactol and form the α-anomer enriched carbohydrate of formula (III). To do this, the lactol of formula (II) is contacted with a base, in a low freezing inert solvent. The temperature of the mixture is then lowered to about −40° C. to about −120° C. and a sulfonating agent is added.

Bases suitable for use in preparing the α-anomer enriched carbohydrate of formula (III) may be selected from the group consisting of triethylamine, trimethylamine, tributylamine, dibutylamine, diethylmethylamine, dimethylethylamine, benzylmethylaminet N-methylmorpholine, tripropylamine, dipropylethylamine, N,N-dimethylbenzylamine, diisopropylethylamine, diethylamine, 1,8-diazabicyclo[5.4.0]undec-7-ene and 1,5-diazabicyclo[4.3.0]non-5-ene. However, the use of a secondary amine base may interfere with the sutfonating reagent, therefore care must be taken to the limit reaction time and maintain low temperatures when secondary amine bases are employed. The base preferably has a pKa of from about 8 to about 20 and the amount of base employed is from about 1 molar equivalent to about 2 molar equivalents and more preferably from about 1.2 molar equivalents to about 1.5 molar equivalents.

The inert solvent should have a freezing point. temperature below −78° C. and is preferably selected from the group consisting of dichloromethane, 1,2-dichloroethane, dichlorofluoromethane, acetone, toluene, anisole, chlorobenzene, and mixtures thereof.

The sulfonating agents suitable for use in preparing the α-anomer enriched carbohydrate of formula (III) are selected from the group consisting of octaflic anhydride, nanoflic anhydride, and trifluoromethanesulfonic anhydride (triflic anhydride), depending on the leaving group desired; preferred is trifluoromethanesulfonic anhydride.

While not wishing to be bound by theory, it is believed that lowering the temperature shifts the α to β anomer ratio of the lactol in favor of the α-anomer from about 1:1 α to β to about 5:1 α to β. For example, a compound of formula (II), where X is benzoyl, was added to dichloromethane and triethylamine at room temperature for 30 minutes and the temperature of the mixture was lowered. An $^9F$ NMR, taken at the various temperatures, showed the increase in the α to β anomer ratio of the lactol at the lower temperatures to be:

| Temperature | α/β Ratio |
| --- | --- |
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The lactol is then trapped in solution at the low temperature and increased α-anomer ratio by adding a sulfonating reagent.

The resulting α-anomer enriched carbohydrate of formula (III) contains a fluoroalkylsulfonyloxy or fluoroarylsulfonyloxy group and as a consequence, is unstable at room temperature. Therefore, the α-anomer enriched carbohydrate of formula (III) is converted to the β-anomer enriched carbohydrate of formula (IV) which contains more stable alkylsulfonyloxy or arylsulfonyloxy leaving groups. The conversion is carried out by contacting the α-anomer enriched carbohydrate of formula (III) with a conjugate anion of a sulfonic acid, in an inert solvent, at elevated temperatures. Sources of conjugate anions of sulfonic acids are known to one of ordinary skill in the art and include:

(a) neutralizing an alkyl or aryl sulfonic acid such as 1-methanesulfonic acid, ethanesulfonic acid, p-toluenesulfonic acid, benzenesulfonic acid, p-bromobenzenesulfonic acid and camphorsulfonic acid, with an alkali metal base such as sodium hydroxide, sodium hydride, potassium hydroxide, potassium t-butoxide, sodium methoxide and the like, forming the alkali metal salt of a sulfonic acid. Examples of conjugate anions of sulfonic acids prepared by this method include alkali metal salts of methane sulfonic acid, ethanesulfonic acid, toluenesulfonic acid, 1-propanesulfonic acid, p-chlorobenzenesulfonic acid, p-bromobenzenesulfonic acid, p-nitrobenzenesulfonic acid, and camphorsulfonic acid; and (b) neutralizing the alkyl or aryl sulfonic acids above with an amine base such as triethylamine, trimethylamine, N,N-dimethylbenzylamine or N-methylmorpholine or with an aromatic nitrogenous base such as pyridine. Examples of salts containing the conjugate anions of sulfonic acids prepared by this method include: trimethylammonium methanesulfonate, triethylammonium methanesulfonate, N,N-dimethylbenzylammonium methanesulfonate, triethylammonium p-chlorobenzenesulfonate, triethylammonium p-bromobenzenesulfonate, tetraethylammonium p-toluenesulfonate, pyridinium methanesulfonate, tetraethylammonium (p-toluene) sulfonate, pyridinium p-toluenesulfonate and pyridinium p-nitrobenzenesulfonate; more preferred is triethylammonium methanesulfonate.

Suitable solvents for use in the conversion of formula (III) must be inert under the conversion conditions; preferred are acetonitrile, 1,1,2-trichloroethane, chlorobenzene, bromobenzene, dichlorobromobenzene, anisole, glyme, diglyme, ethyl acetate, toluene, xylenes, pyridine, N-methylpyrrolidinone, N,N-dimethylformamide, 1,3-dimethyl-2-imidazolone, N,N-dimethylacetamide, and mixtures thereof; most preferred are anisole, toluene, glyme, acetonitrile, and mixtures thereof.

The $\beta$-anomer enriched carbohydrate of formula (IV) that results from the conversion is more stable than flourinated $\alpha$-anomer enriched carbohydrate of formula (III) and therefore is less reactive. Moreover, as a $\beta$-anomer, the carbohydrate of formula (III) contains the wrong stereochemistry for $S_N2$ coupling. As such, the $\beta$-anomer carbohydrate of formula (IV) must be converted to the corresponding $\alpha$-anomer carbohydrate of formula (V). This conversion is accomplished by an equilibration which involves heating the $\beta$-anomer carbohydrate of formula (IV) in the presence of a conjugate anion of a sulfonic acid, at temperatures ranging from about 50° C. to about 120° C., for about 18 hours to about 72 hours. The conjugate anion of a sulfonic acid employed may be the same as that used in the conversion of the $\beta$-anomer enriched carbohydrate of formula (III) or derived from a separate source.

The nucleobase anions of formula (VI) employed herein are commonly known to organic chemist and no discussion of their synthesis is necessary. However, before they can be coupled with $\alpha$-anomer carbohydrate of formula (V), the amino and/or hydroxy groups of the nucleobase anion (or it's tautomeric equivalent) of formula (IV) are preferably blocked by protecting groups. The protecting groups prevent the amino and/or hydroxy groups from providing a competing reaction site for the $\alpha$-anomer carbohydrate of formula (V) during coupling. The amino protecting groups (W) and/or hydroxy protecting groups (Z) chosen depend on the nature of the specific nucleobase selected. The protecting groups are attached to the nucleobase before it is converted to a nucleobase anion and are removable subsequent thereto.

Preferred amino protecting groups (W) are selected from the group consisting of alkylcarboxamides, haloalkylcarboxamides and arylcarboxamides such as trichloroethoxycarbonyl, trifluoroacetyl, naphthoyl, formyl, acetyl; sulfonamides such as alkylsulfonamido and arylsulfonamido, and more preferred is pivaloyl. In addition to serving as an amino protecting group, the pivalamido protecting group increases the solubility of notoriouslyinsoluble purine nucleobase derivatives and directs the N-glycosidic coupling such that the 9 regioisomer is formed in preference to the 7 regioisomer.

Preferred hydroxy protecting groups (Z) for the nucleobase are selected from the group consisting of ether forming groups such as benzyl, t-butyl, trityl, tetrahydropyranyl, tetrahydrofuranyl, methoxymethyl, trityl; esters such as formyl, acetylpropionyl, pivaloyl, benzoyl, substituted benzoyl; carbonates such as carbobenzoxy, t-butoxycarbonyl, carbethoxy, vinyloxycarbonyl; carbamates, such as N,N-dialkylcarbamoyl; trialkylsilyl ethers such as t-butyltrimethylsilyl, t-hexyldimethylsilyl, triisopropylsilyl; more preferred is pivaloyl.

In addition, it is often advisable to convert any keto oxygen atoms on the nucleobase to a protected enol form. This makes the nucleobase more nucleophilic and enhances the reactivity of the nucleobase.

Procedures for attaching protecting groups to nucleobases are described in U.S. Pat. No. 4,526,988.

The nucleobase is converted to a metal salt anion before coupling to enhance its reactivity with the $\alpha$-anomer enriched carbohydrate of formula (V). The nucleobase anion of formula (VI) is formed by adding a base to the nucleobase in an inert solvent. The bases may be selected from the group consisting of sodium t-butoxide, potassium hydroxide, potassium-t-butoxide, potassium ethoxide, potassium methoxide, sodium ethoxide, sodium methoxide, sodium hydride, lithium hydride and potassium hydride. Alternatively the base may be a trialkylamine or a tetraalkylammonium hydroxide or alkoxide. The inert solvent may be selected from the group consisting of acetonitrile, dimethylformamide, dimethylacetamide, 1,3-dimethyl-1-2-imidazolidinone, N-methylpyrrolidinone, sulfolane, tetrahydrofuran, dimethylsulfoxide, and mixtures thereof. The solvent may either be removed prior to the coupling reaction or admixed with the reaction solvent, provided the admixture is inert to the coupling reaction.

In the present process, at least an equimolar amount of nucleobase anion of formula (VI) is employed, relative to the amount of $\alpha$-anomer enriched carbohydrate of formula (V) employed. However, it is more preferable to use an excess of nucleobase anion ranging from about 2 equivalents to about 10 equivalents.

The $\alpha$-anomer carbohydrate of formula (V) is coupled with the nucleobase anion of formula (VI) in inert solvent and heated to form the nucleoside compound of formula (I).

Solvents suitable for use in the coupling must be inert to the coupling reaction conditions. Preferred solvents are selected from the group consisting of dichloromethane, 1,2-dichloroethane, dichlorofluoromethane, acetone, toluene, anisole, chlorobenzene, dimethylformamide, acetonitrile, N,N-dimethylacetamide, methanol, tetrahydrofuran, ethyl acetate, dimethoxymethane, 1,2-dimethoxyethane, dimethylsulfoxide, and mixtures thereof.

The temperatures employed in the coupling reaction range from 23° C. to about 170° C.; more preferably from about 23° C. to about 130° C., and most preferably from about 23° C. to about 50° C. The coupling is preferably carried out under atmospheric conditions and is substantially complete in about 5 minutes to about 24 hours.

An advantage of the present process is that the process steps may be carried out sequentially in separate processing vessels or in one step in a single processing vessel (one pot).

Although not critical, it is advisable that the coupling reaction be carried out in a dry atmosphere, e.g., in the presence of dry air, nitrogen, or argon, since certain nucleobase anions are moisture sensitive.

The progress of the present process may be monitored by procedures well known to one of ordinary skill in the art such as high pressure liquid chromatography (HPLC) and thin layer chromatography (TLC) which detect the presence of nucleoside product.

In accordance with the present process, the β-anomer enriched nucleosides of formula (I) are prepared in an α to β anomer ratio ranging from greater than 1:1 to about 1:5.

The β-anomer enriched nucleosides of the present process may be isolated by the procedure described by Chou, in U.S. Pat. No. 4,965,374, which is incorporated herein by reference, or by conventional methods known to those of ordinary skill in the art such as chromatography, extraction or crystallization.

The following example illustrates specific aspects of the present invention and is not intended to limit the scope thereof in any respect and should not be so construed.

EXAMPLE

9-[1-(2'-deoxy-2',2'-difluoro-3',5'-di-O-benzoyl-D-ribofuranosyl)]-2,6-dipivalamido purine To 2-deoxy-2,2-difluoro-D-ribofuranosyl-3,5-dibenzoate (2.0 g) was added triethylamine (536 ml) and dichloromethane (20 ml) which was stirred at room temperature for 30 minutes. After, the mixture was cooled to −78° C., trifluoromethanesulfonyl anhydride (1.49 g) was added and the mixture was again stirred for 15 minutes, whereupon the potassium salt of bromobenzenesulfonate (1.5 g) was added. The mixture was allowed to warm to 0° C. and in acetonitrile (25 ml) under a nitrogen atmosphere heated for 3 hours to a temperature of 110° C. to form 2-deoxy-2,2-difluoro-D-ribofuranosyl-3,5-dibenzoyl-1-(p-bromobenzene)sulfonate in a 2.8:1 α to β anomer ratio. To 2-deoxy-2,2-difluoro-D-ribofuranosyl-3,5-dibenzoyl-1-(p-bromobenzene)sulfonate (2.64 moles) was added the potassium salt of dipivalamidopurine (1.88 g) in acetonitrile. The mixture was then heated to 70° C. for 17 hours to form the above product.

The above product was isolated by adding ethylacetate (25 ml), ice (1 ml) and saturated aqueous sodium chloride solution (2 ml) to the resulting reaction mixture. After removing the ethylacetate, the mixture washed with saturated aqueous sodium carbonate (5 ml), saturated sodium chloride (5 ml), dried over magnesium sulfate and concentrated.

The above product was purified by flash chromatography over silica (50 g) eluted with a 25/75 ethylacetate/toluene solution, followed by a 50/50 ethylacetate/toluene solution. 1.03 g of the above product was obtained in an overall yield of 57.5 percent.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective process for preparing a β-anomer enriched 2-deoxy-2',2'-difluoronucleoside of the formula

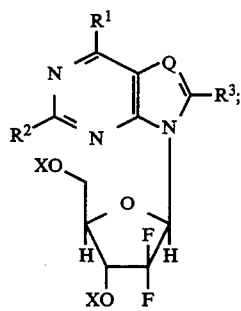

wherein each X is independently selected from hydroxy protecting groups; R¹, R² and R³ are each independently selected from the group consisting of hydrogen, —OZ, —NHW, N(alkyl)W, halo, cyano, azido, alkoxy and thioalkyl; Q is selected from the group consisting of CH, CR₄ and N, wherein R₄ is halo, carboxamide, thiocarboxamide, alkoxycarbonyl and nitrile; where Z is a hydroxy protecting group and W is an amino protecting group; comprising (a) contacting a lactol of the formula

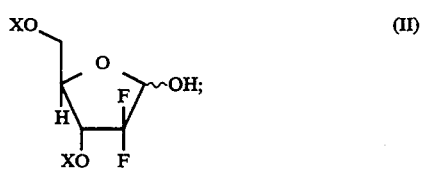

wherein X is as defined above; with a base in a low freezing inert solvent; lowering the temperature of the reaction mixture in the range of about −40° C. to about −120° C.; and adding a sulfonating reagent to form an α-anomer enriched carbohydrate of the formula

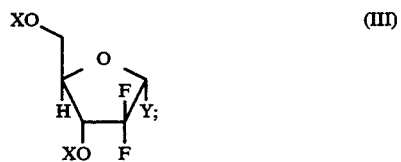

wherein y is as defined above and Y is a fluoroalkylsulfonyloxy or fluoroarylsulfonyloxy group;

(b) contacting the carbohydrate of formula (III) with a conjugate anion of a sulfonic acid, in a inert solvent, while the temperature of the reaction mixture is allowed to increase to be in the range of about 0° C. to about 25° C. to form a β-anomer enriched carbohydrate of the formula

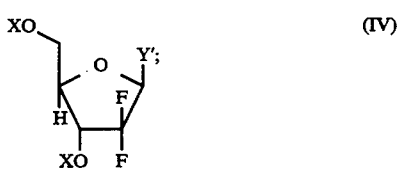

wherein X is as defined above and Y' is an alkylsulfonyloxy or arylsulfonyloxy group;

(c) heating to a temperature of about 50° C. to about 120° C. for a time sufficient to form an α-anomer enriched carbohydrate of the formula

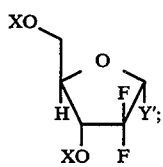

wherein X and Y' are as defined above;
(d) contacting the carbohydrate of formula (V) with an nucleobase anion of the formula

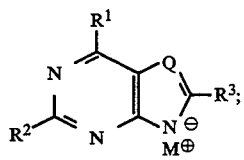

wherein $R^1$, $R^2$, $R^3$ and Q are as defined above; and M is a metal cation; in an inert solvent; and
(e) heating to a temperature ranging from about 23° C. to about 170° C. for a time sufficient to form the β-anomer enriched 2-deoxy-2',2'-difluoronucleoside of formula (I).

2. The process of claim 1, wherein the sulfonating reagent is a fluoroalkylsulfonyl anhydride or fluoroarylsulfonyl anhydride.

3. The process of claim 2, wherein the sulfonating reagent is selected from the group consisting of octaflic anhydride, nanoflic anhydride, triflic anhydride.

4. The process of claim 1 wherein the conjugate anion of a sulfonic acid is selected from the group consisting of alkali metal salts of sulfonic acids and amine salts of sulfonic acids.

5. The process of claim 4 wherein the alkali metal salt of a sulfonic acid is selected from the group consisting of methanesulfonic acid, ethanesulfonic acid, p-toluenesulfonic acid, 1-propanesulfonic acid, p-chlorobenzenesulfonic acid, p-bromobenzenesulfonic acid, p-nitrobenzenesulfonic acid and camphorsulfonic acid.

6. The process of claim 4 wherein the amine salt of a sulfonic acid is selected from the group consisting of amine salts of trimethylammonium methanesulfonate, triethylammonium methanesulfonate, N,N-dimethylbenzylammonium methanesulfonate, triethylammonium (p-chlorobenzene) sulfonate, triethylammonium (p-bromobenzene) sulfonate, pyridinium methanesulfonate, tetraethylammonium p-toluenesulfonate, pyridinium toluenesulfonate and pyridinium nitrobenzenesulfonate.

7. The process of claim 1 wherein the heating in step (c) is carried out to a temperature of from about 30° C. to about 130° C.

8. The process of claim 1 wherein M is sodium or potassium.

9. The process of claim 1 wherein the solvent is selected from the group consisting of dichloromethane, 1,2-dichloroethane, dichlorofluoromethane, acetone, toluene, anisole, chlorobenzene, dimethylformamide, acetonitrile, N,N-dimethylacetamide, methanol, tetrahydrofuran, ethyl acetate, dimethylsulfoxide, and mixtures thereof.

10. The process of claim 9 wherein the solvent is selected from dichloromethane and acetonitrile.

11. A stereoselective process for preparing a β-anomer enriched carbohydrate of the formula

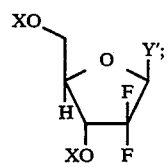

wherein each X is independently selected from hydroxy protecting groups; and Y' is an alkylsulfonyloxy or arylsulfonyloxy group; comprising contacting a compound of the formula

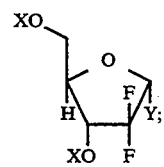

wherein X is as defined above and Y is a fluoroalkylsulfonyloxy or fluoroarylsulfonyloxy group; with the conjugate anion of a sulfonic acid, in an inert solvent, at elevated temperatures.

12. A stereoselective process for preparing α-anomer enriched 2-deoxy-2',2'-difluoro-D-ribofuranosyl-3,5-hydroxy protected-1-alkyl and aryl sulfonate intermediates of the formula

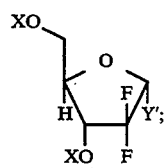

wherein each X is independently selected from hydroxy protecting groups; and Y' is an alkylsulfonyloxy or arylsulfonyloxy group; comprising contacting an α-anomer enriched carbohydrate of the formula

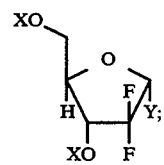

wherein X is as defined above and Y is a fluoroalkylsulfonyloxy or fluoroarylsulfonyloxy group; with a conjugate anion of a sulfonic acid, in a inert solvent, while the temperature is allowed to rise to a range of about 0° C. to about 25° C., to form a β-anomer enriched carbohydrate of the formula

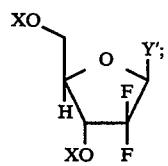

wherein X and Y' are as defined above; heating to a temperature of about 50° C. to about 120° C. for a time sufficient to form an α-anomer enriched ribofuranosyl of formula (V).

* * * * *